(12) United States Patent
Liu et al.

(10) Patent No.: US 10,004,595 B2
(45) Date of Patent: Jun. 26, 2018

(54) ACCOMMODATING INTRAOCULAR LENS

(71) Applicant: NOVARTIS AG, Basel (CH)

(72) Inventors: Jian Liu, Fort Worth, TX (US);
Stephen J. Van Noy, Southlake, TX (US); Yin Yang, Arlington, TX (US)

(73) Assignee: Novartis AG, Basel (CH)

( * ) Notice: Subject to any disclaimer, the term of this patent is extended or adjusted under 35 U.S.C. 154(b) by 33 days.

(21) Appl. No.: 15/372,936

(22) Filed: Dec. 8, 2016

(65) Prior Publication Data
US 2017/0172732 A1 Jun. 22, 2017

Related U.S. Application Data

(60) Provisional application No. 62/270,698, filed on Dec. 22, 2015.

(51) Int. Cl.
A61F 2/16 (2006.01)

(52) U.S. Cl.
CPC .......... *A61F 2/1624* (2013.01); *A61F 2/1635* (2013.01); *A61F 2/1694* (2013.01); *A61F 2002/169* (2015.04); *A61F 2002/1681* (2013.01); *A61F 2002/1682* (2015.04); *A61F 2002/16901* (2015.04); *A61F 2002/16902* (2015.04); *A61F 2250/0003* (2013.01)

(58) Field of Classification Search
CPC ............ A61F 2/1635; A61F 2002/1682; A61F 2/1624; A61F 2/1648; A61F 2/1694; A61F 2250/0003; A61F 2002/169; A61F 2002/16901; A61F 2002/16902
See application file for complete search history.

(56) References Cited

U.S. PATENT DOCUMENTS

2008/0269887 A1  10/2008  Cumming
2014/0180403 A1   6/2014  Silvestrini et al.

FOREIGN PATENT DOCUMENTS

WO   2013/187497 A1   12/2013

*Primary Examiner* — David H Willse
*Assistant Examiner* — Javier Blanco

(57) ABSTRACT

An accommodating IOL includes a flexible optic membrane, a flexible skirt extending from an outer periphery of the flexible optic membrane and defining an outer periphery of the accommodating IOL, and a capsular contact ring configured to be positioned anterior to the flexible optic membrane and having a diameter less than a diameter at the outer periphery of the accommodating IOL. The accommodating IOL further includes a plurality of strut assemblies connecting the capsular contact ring and flexible skirt. When the capsular bag transitions from an accommodative state to a disaccomadative state, the capsular bag exerts a force on the capsular contact ring, at least a portion of that force being transferred to the flexible skirt by the plurality of strut assemblies. The transferred force causes a flattening of the flexible optic membrane in a manner that reduces the optical power of the accommodating IOL.

5 Claims, 5 Drawing Sheets

ACCOMMODATING INTRAOCULAR LENS

FIELD

This present disclosure relates generally to the field of intraocular lenses (IOLs) and, more particularly, to accommodating IOLs.

BACKGROUND OF THE DISCLOSURE

Cataract, or clouding of the natural lens of the eye, is the leading cause of preventable blindness in the world. Presently, cataracts are treated by surgical removal of the affected lens and replacement with an artificial intraocular lens ("IOL"). FIG. 1 is a diagram of an eye 100 illustrating anatomical structures related to the surgical removal of a cataract and the implantation of an IOL. The eye 100 comprises a lens 102, an optically clear cornea 104, and an iris 106. A lens capsule (capsular bag 108) located behind the iris 106 of the eye 100 contains the lens 102. More particularly, the lens 102 is seated between an anterior capsule segment (anterior capsule 110) and a posterior capsular segment (posterior capsule 112). The anterior capsule 110 and the posterior capsule 112 meet at an equatorial region 114 of the capsular bag 108. The eye 100 also comprises an anterior chamber 116 located in front of the iris 106 and a posterior chamber 118 located between the iris 106 and the capsular bag 108.

A common technique for cataract surgery (including removal of an opacified lens 102) is extracapsular cataract extraction ("ECCE"). ECCE involves the creation of an incision near the outer edge of the cornea 104 and an opening in the anterior capsule 110 (i.e., an anterior capsulotomy) through which the opacified lens 102 is removed. The lens 102 can be removed by various known methods. One such method is phacoemulsification, in which ultrasonic energy is applied to the lens to break it into small pieces that are aspirated from the capsular bag 108. Thus, with the exception of the portion of the anterior capsule 110 that is removed in order to gain access to the lens 102, the capsular bag 108 may remain substantially intact throughout an ECCE. The intact posterior capsule 112 provides a support for the IOL and acts as a barrier to the vitreous humor within the posterior chamber 120 of the eye 100. Following removal of the opacified lens 102, an artificial IOL may be implanted within the capsular bag 108 through the opening in the anterior capsule 110. Implanted IOLs are typically monofocal lenses that provide a suitable focal power for distance vision but require the use a pair of spectacles or contact lenses for near vision. Multifocal IOLs relying on diffractive patterns to generate multiple foci, are also available but to date have not been widely accepted.

In a healthy eye, zonular forces are exerted by ciliary muscles 122 and attached zonules 124 surrounding the periphery of the capsular bag 108. These forces change the shape of the natural lenses, thereby changing its power and allowing a clear focus on an image as its distance varies. When monofocal or diffractive multifocal IOLs are implanted, this natural accommodative ability of the eye is lost.

Therefore, a need exists for a safe and stable accommodative intraocular lens that provides accommodation over a broad and useful range.

SUMMARY OF THE DISCLOSURE

The present disclosure concerns accommodating IOLs that may be implanted in the capsular bag of a patient's eye and are configured to harness the energy of the movement of the capsular bag upon contraction and relaxation of the ciliary muscles. In certain embodiments, an accommodating IOL includes a flexible optic membrane configured to be placed along the optical axis of the patient's eye, a flexible skirt extending from an outer periphery of the flexible optic membrane and defining an outer periphery of the accommodating IOL, and a capsular contact ring configured to be positioned along the optical axis of the patient's eye anterior to the flexible optic membrane (the capsular contact ring having a diameter less than a diameter at the outer periphery of the accommodating IOL). The accommodating IOL further includes a plurality of strut assemblies connecting the capsular contact ring and flexible skirt. When the capsular bag transitions from an accommodative state to a disaccomadative state, the capsular bag exerts a force on the capsular contact ring, at least a portion of that force being transferred to the flexible skirt by the plurality of strut assemblies. The transferred force causes a flattening of the flexible optic membrane in a manner that reduces the optical power of the accommodating IOL.

Certain embodiments of the present disclosure may provide one or more technical advantages. For example, the capsular contact ring, flexible skirt, and strut assemblies may provide the ability to efficiently harness ciliary process energy in order to drive the change in shape of the flexible optic membrane. As a result, a relatively large accommodative range may be provided.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

Figure 1:
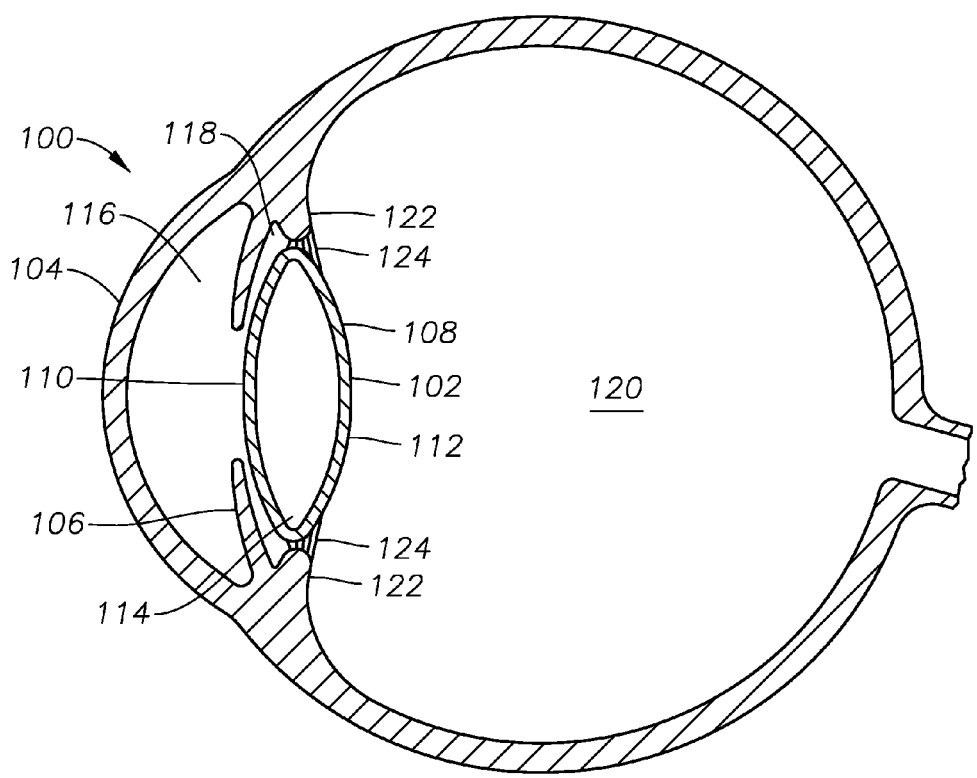
FIG. 1 is a diagram of an eye illustrating anatomical structures related to the surgical removal of a cataract and the implantation of an IOL.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure generally relates to an intraocular lens (IOL) configured to be implanted in the capsular bag 108 of a patient's eye 100 and configured to harness the energy of the movement of the capsular bag 108 upon contraction and relaxation of the ciliary muscles 122. As described in detail below, the energy of the movement of the capsular bag 108 may be harnessed, at least in part, by a capsular contact ring positioned anterior to the flexible optic membrane of the IOL and connected to a flexible skirt surrounding the flexible optic membrane via a plurality of strut assemblies. The harnessed energy may result in a change in the optical power of the IOL.

Figure 2A:
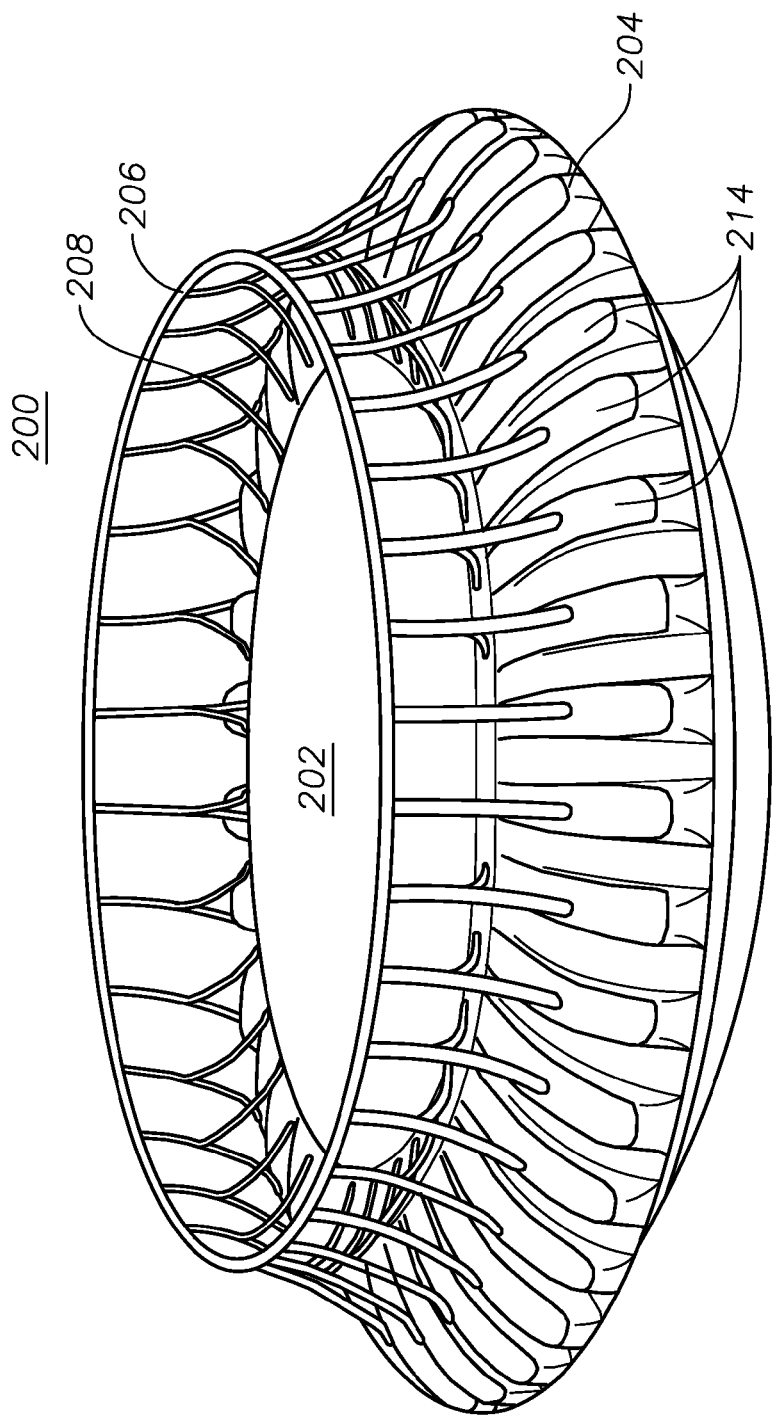
FIGS. 2A-2B is an exemplary accommodating IOL, according to certain embodiments of the present disclosure.
Figure 2B:
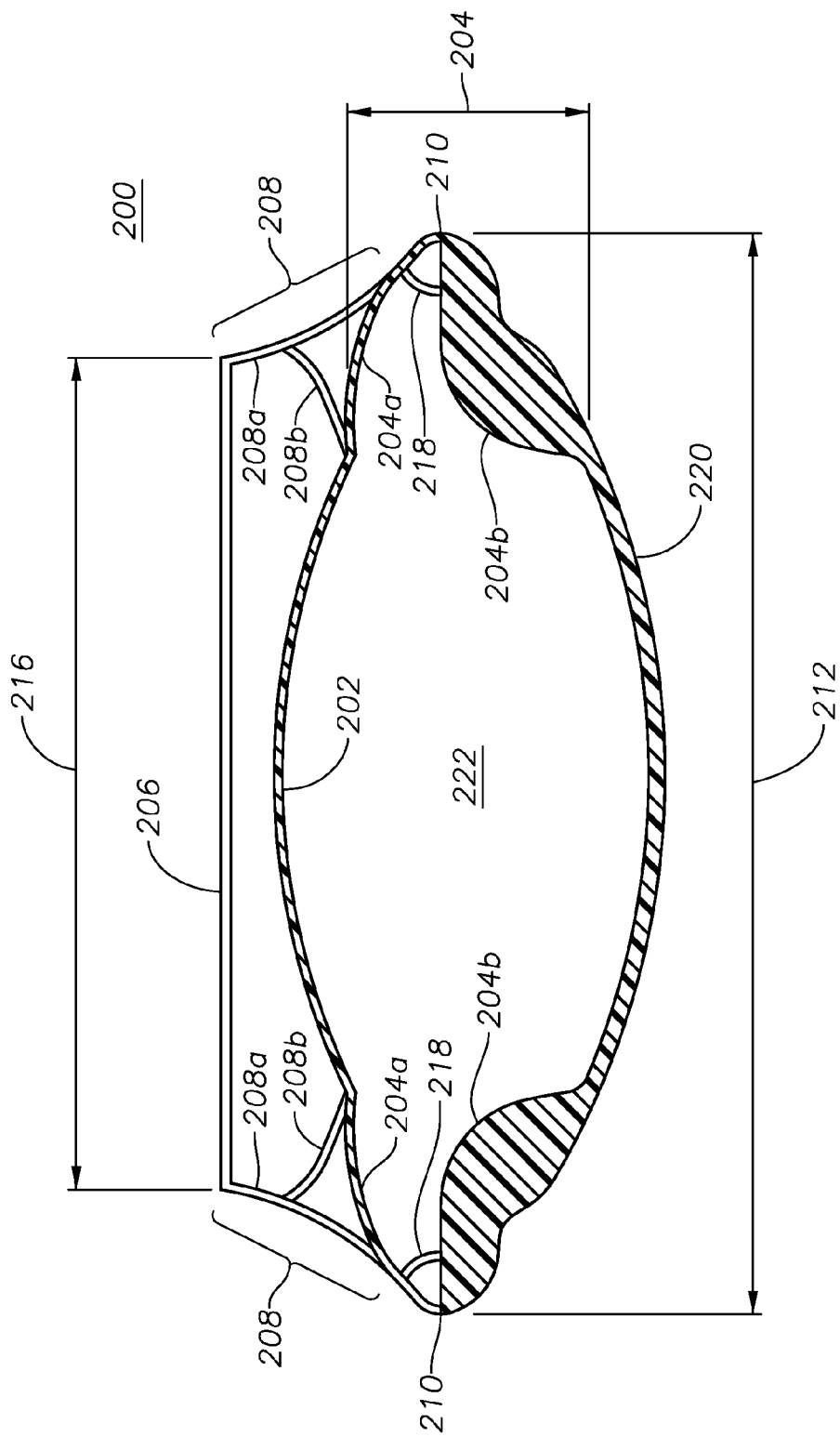

FIGS. 2A-2B illustrate an exemplary accommodating IOL 200, according to certain embodiments of the present disclosure. In general, accommodating IOL 200 includes a flexible optic membrane 202, a flexible skirt 204 extending from an outer periphery of the flexible optic membrane 202, and a capsular contact ring 206. The capsular contact ring 206 is connected to the flexible skirt via a plurality of strut assemblies 208. When the capsular bag 108 in which accommodating IOL 200 is implanted transitions from an accommodative state to a disaccomadative state, the capsular bag 108 may exert a force on the capsular contact ring 206. At least a portion of that force may be transferred to the flexible skirt 204 by the plurality of strut assemblies 208, thereby causing radial expansion of the flexible skirt 204 and a flattening of the flexible optic membrane 202. The flattening of the flexible optic membrane 202 may result in a reduction in the optical power of the accommodating IOL 200.

Flexible optic membrane 202 may include any suitable structure that, alone or in combination with other elements of accommodating IOL 200, provides an optical power for accommodating IOL 200. In certain embodiments, flexible optic membrane 202 may have a diameter in the range of 2 mm to 8 mm and a radius of curvature in the range of 3.4 mm to 200 mm (each of which may be variable within those ranges, as described in further detail below). Additionally, flexible optic membrane 202 may have a thickness in the range of 11 µm to 25 µm. In certain embodiments, the optical power provided by flexible optic membrane 202 (alone or in combination with other elements of accommodating IOL 200) may be variable, the variation resulting at least in part from a change in the radius of curvature of the flexible optic membrane 202 (e.g., in response to forces exerted by the capsular bag 108, as described in further detail below).

Flexible skirt 204 may extend radially from a periphery of flexible optic membrane 202 and may define an outer periphery 210 of accommodating IOL 200 having a diameter 212. More particularly, flexible skirt 204 may comprise (1) an anterior portion 204a that extends from the flexible optic membrane 202 to the outer periphery 210, and (2) a posterior portion 204b the extends posteriorly from the outer periphery 210. In certain embodiments, anterior portion 204a may have a thickness the same or nearly the same as the thickness of flexible optic membrane 202. Additionally, posterior portion 204b may have a greater thickness that anterior portion 204a in order to provide structural stability for accommodating IOL 200.

In certain embodiments, flexible skirt 204 may have a structure facilitating radial expansion at the junction between the flexible skirt 204 and the flexible optic membrane 202, thereby facilitating an increase in the diameter of flexible optic membrane 202 and a corresponding increase in the radius of curvature of flexible optic membrane 202. For example, flexible skirt 204 may comprise a plurality ribs 214, all or a portion of which may be formed in anterior portion 204a.

In certain embodiments, flexible skirt 204 may include one or more sharp edge features configured to contact capsular bag 108. These sharp edge features may help to inhibit migration of lens epithelial cells from the equatorial region 114 of the capsular bag 108, thereby aiding in the prevention of posterior capsule opacification (PCO).

Capsular contact ring 206 may be a substantially circular structure position anterior to flexible optic membrane 202. In certain embodiments, capsular contact ring 206 may have a diameter 216 greater than that of flexible optic membrane 202 to prevent interference with a patient's vision when accommodating IOL 200 is implanted in the capsular bag 108 of the patient's eye 100. Additionally, the diameter 216 of capsular contact ring 206 may be less than the diameter 212 at the outer periphery 210 of accommodating IOL 200.

Capsular contact ring 206 may be configured, when implanted in the capsular bag 108 of a patient's eye 100, to engage a region of the anterior capsule 110. As the eye transitions from a disaccomadative state to an accommodative state (and vice versa), this engagement may allow forces exerted by the capsular bag 108 to be transferred to accommodating IOL 200 (as described in further detail below).

Capsular contact ring 206 may be coupled to flexible skirt 204 via a plurality of strut assemblies 208. Strut assemblies 208 may each comprise a primary strut 208a and a secondary strut 208b. Primary strut 208a of each strut assembly 208 may extend from the capsular contact ring 206 and connect to a point on the flexible skirt 204. For example, each primary strut 208a may connect to the flexible skirt 204 at a corresponding one of ribs 214. Secondary strut 208b of each strut assembly 208 may extend from the primary struts 208a and connect to a point on the flexible skirt 204. For example, each secondary strut 208b may connect to the flexible skirt 204 at a corresponding one of ribs 214. Moreover, the point of connection for secondary strut 208b may be between the point of connection of the primary strut 208a and the flexible optic membrane 202. In certain embodiments, primary struts 208a and secondary struts 208b may each have a radius of curvature (as depicted in FIGS. 2A-2B); however, any other suitable shape is contemplated by the present disclosure.

In certain embodiments, accommodating IOL 200 may additionally include a plurality of internal support members 218, each internal support member corresponding to one of the plurality of strut assemblies 208. Each internal support member 218 may extend from a posterior surface of the anterior segment 204a of flexible skirt 204 and connect to an anterior surface of the posterior portion 204b of flexible skirt 204. Internal support members 218 may increase the efficiency with which force is transferred from the capsular bag 108 to the accommodating IOL 200 to achieve a change in the radius of curvature of flexible optic membrane 02.

In certain embodiments, accommodating IOL 200 may additionally a posterior optic 220 extending from the inner diameter defined by posterior portion 204b of flexible skirt 204. In other words, flexible optic membrane 202, flexible skirt 204, and posterior optic 220 may collectively form a sealed chamber 222, which may contain a fluid. For example, the fluid in sealed chamber 222 may comprise any suitable polymeric material (e.g., silicone, silicone oil, or any other suitable fluidic medium) that is preferably of gel-like consistency, bubble free, optically clear, sterile, and biocompatible. Moreover, flexible optic membrane 202, posterior optic 220, and the fluid contained in chamber 222 may collectively provide the total optic power of accommodating IOL 200. In certain embodiments, posterior optic 220 may comprise a rigid optic that remains substantially undeformed in response to forces exerted by the capsular bag 108. In certain other embodiments, posterior optic 220 may comprise a flexible optic similar to flexible optic membrane 202. In such embodiments, a radius of curvature of posterior optic 220 may change in response to forces exerted by the capsular bag 108, the change in curvature of both flexible optic membrane 202 and posterior optic 220 collectively resulting in the total power change of accommodating IOL 200. However, even in embodiments in which posterior optic 220 is a flexible optic, little or no change in the radius of curvature may result from forces exerted by the capsular bag 208 due to the relatively rigid structure of the posterior portion 204b of flexible skirt 204.

In certain embodiments, the above-described components of accommodating IOL 200 may each comprise a variety of materials that include, for example, fluid impermeable and biocompatible materials. In particular, the flexible optic membrane 202 and the posterior optic 220 may each be constructed of materials that are optically transparent and smooth (e.g., an optical-quality surface). Exemplary materials include hydrogels, silicones, acrylic materials, and other elastomeric polymers and soft plastics. For example, the silicone materials can be unsaturated terminated siloxanes, such as vinyl terminated siloxanes or multi-vinyl terminated siloxanes. Non-limiting examples include vinyl terminated diphenylsiloxane-dimethylsiloxane copolymers, vinyl terminated polyphenylmethylsiloxanes, vinyl terminated phenylmethylsiloxane-diphenyidimethylsiloxane copolymers, vinyl terminated polydimethylsiloxanes and methacrylate, and acrylate functional siloxanes. As another example, the hydrogel or hydrophobic acrylic materials may include materials such as the AcrySof® acrylic. The above-described components of accommodating IOL 200 may each may each be constructed of the same material (cast as a single piece or assembled from multiple pieces). Alternatively, the above-described components of accommodating IOL 200 may be formed of any suitable combination of different materials.

Figure 3A:
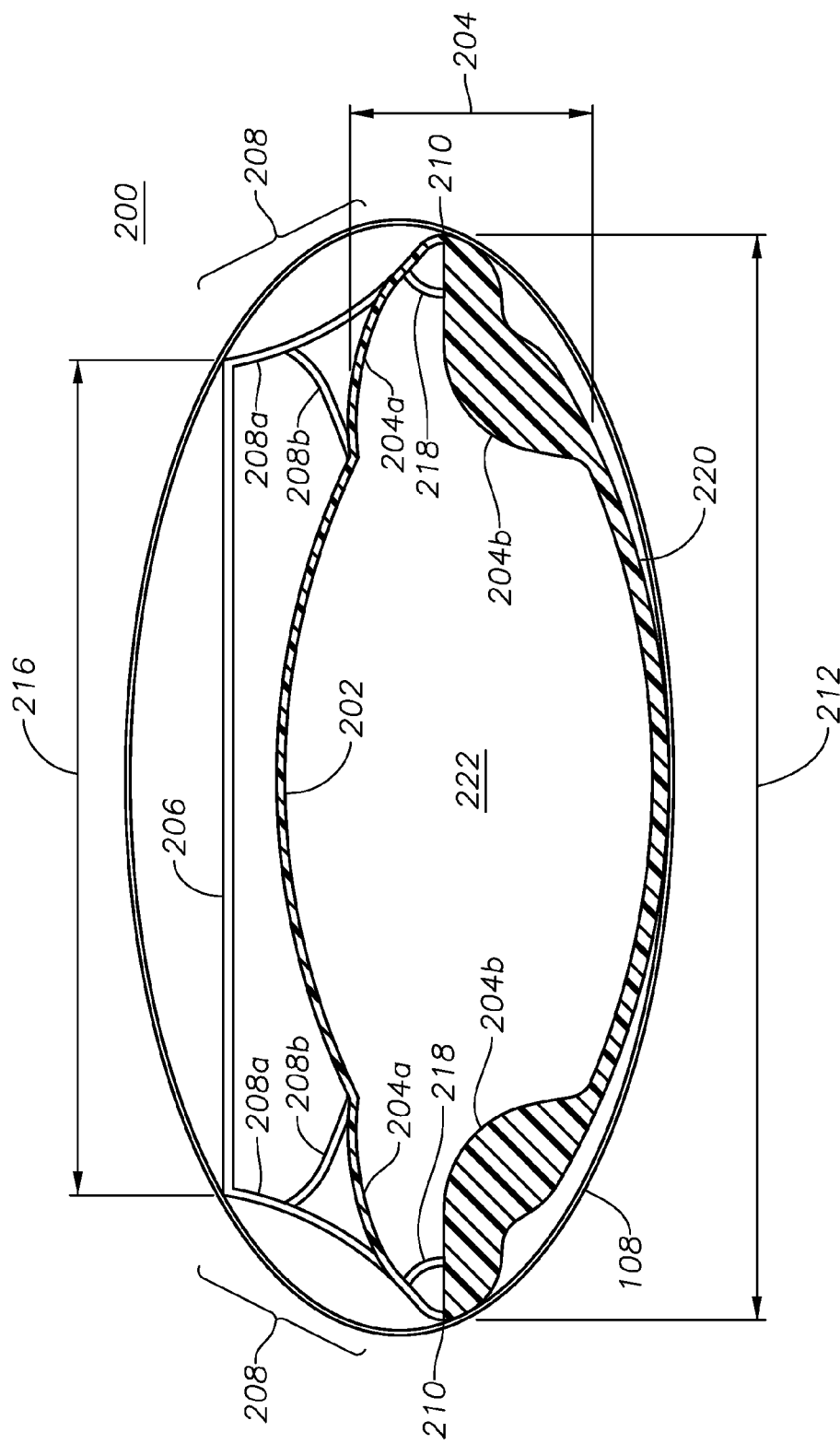
FIGS. 3A-3B illustrate the deformation of the accommodating IOL depicted in FIGS. 2A-2B as the capsular bag transitions from an accommodative state to a disaccomadative state, according to certain embodiments of the present disclosure The skilled person in the art will understand that the drawings, described below, are for illustration purposes only. The drawings are not intended to limit the scope of the applicant's teachings in any way.
Figure 3B:
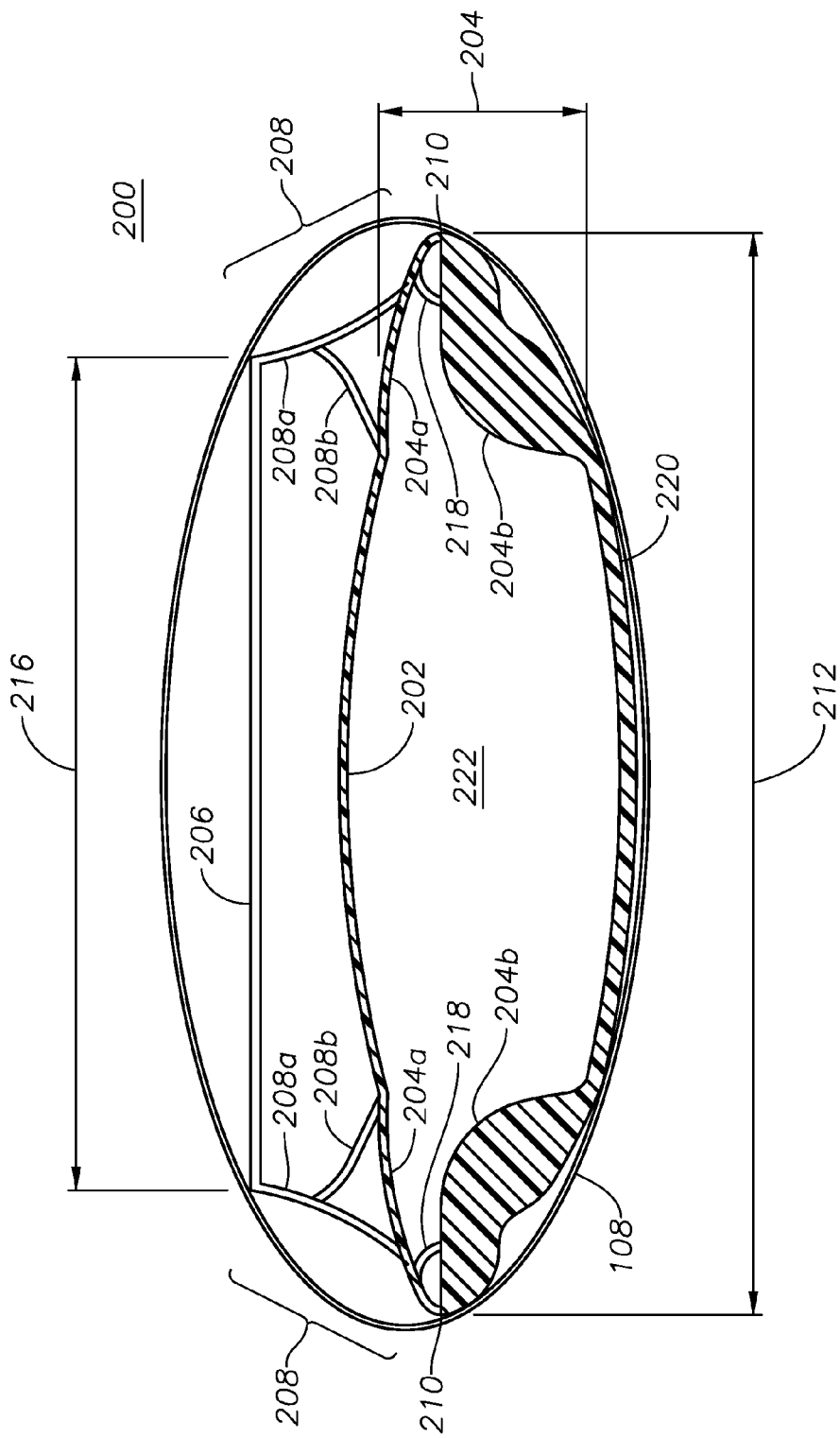

FIGS. 3A-3B illustrate the deformation of accommodating IOL 200 as the capsular bag 108 transitions from an accommodative state to a disaccomadative state, according to certain embodiments of the present disclosure. More particularly, FIG. 3A depicts accommodating IOL 200 is capsular bag 108 when capsular bag 108 is in an accommodative state while FIG. 3B depicts accommodating IOL 200 is capsular bag 108 when capsular bag 108 is in a disaccomadative state.

As capsular bag 108 transitions for the accommodative state to the disaccomadative state, the capsular bag may flatten axially. This flattening may cause a compressive force to be applied to accommodating IOL 200 and in particular to capsular contact ring 206. This force may be transferred from capsular contact ring 206 to flexible skirt 204 by strut assemblies 208 this transferred force may cause radial expansion of the flexible skirt 204. Such radial expansion may stretch flexible optic membrane radially, thereby increasing the radius of curvature of flexible optic membrane 202. This increase in the radius of curvature may reduce the overall optical power of accommodating IOL 200, allowing for a range of vision.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:
1. An accommodating intraocular lens (IOL) configured to be implanted within a capsular bag of a patient's eye, the lens comprising:
a flexible optic membrane configured to be placed along the optical axis of the patient's eye;
a flexible skirt extending from an outer periphery of the flexible optic membrane, the flexible skirt defining an outer periphery of the accommodating IOL and comprising an anterior portion extending radially outward from the outer periphery of the flexible optic membrane to the outer periphery of the accommodating IOL and a posterior portion extending posteriorly from the outer periphery of the accommodating IOL, the anterior portion and the posterior portion connected at the outer periphery of the accommodating IOL;
a posterior optic extending from the posterior portion of the flexible skirt, the flexible optic membrane, the flexible skirt, and the posterior optic collectively defining a sealed chamber containing a fluid;
a capsular contact ring positioned anterior to the flexible optic membrane, the capsular contact ring configured to be positioned along the optical axis of the patient's eye and in contact with an inner surface of the anterior capsule of the patient's eye, the capsular contact ring having a diameter less than a diameter at the outer periphery of the accommodating IOL, the diameter of the capsular contact ring being greater than a diameter at the outer periphery of the flexible optic membrane;
a plurality of strut assemblies connecting the capsular contact ring and the anterior portion of the flexible skirt, each of the plurality of strut assemblies comprising (i) a primary strut extending from the capsular contact ring to a first point on the anterior portion of the flexible skirt; and (ii) a secondary strut extending from a second point on the anterior portion of the flexible skirt to the primary strut, the second point being located between the first point and the flexible optic membrane;
wherein, when the capsular bag transitions from an accommodative state to a disaccomodative state, the capsular bag exerts a force on the capsular contact ring, at least a portion of that force being transferred to the flexible skirt by the plurality of strut assemblies, the transferred force causing a flattening of the flexible optic membrane in a manner that reduces the optical power of the accommodating IOL,
wherein the force transferred to the flexible skirt by the plurality of strut assemblies causes radial expansion of the flexible skirt at the junction between the flexible skirt and the flexible optic membrane, the radial expansion of the flexible skirt causing a corresponding radial expansion at the outer periphery of the flexible optic membrane,
wherein the flexible optic membrane comprises a thickness in the range of 11 μm to 25 μm, and a diameter at its outer periphery in the range of 2 mm to 8 mm, wherein the flexible optic membrane, the posterior optic, and the fluid contained within the sealed chamber collectively provide the total optic power of the accommodating IOL.

2. The accommodating IOL of claim 1, wherein the flexible skirt comprises a plurality of ribs.

3. The accommodating IOL of claim 2, wherein each of the plurality of strut assemblies is connected to the flexible skirt at a corresponding one of the plurality of ribs.

4. The accommodating IOL of claim 1, wherein the flexible skirt comprises a plurality of internal support members, each internal support member extending from the posterior portion of the flexible skirt to the anterior portion of the flexible skirt.

5. The accommodating IOL of claim 1, wherein the fluid comprises one of silicone and silicone oil.

* * * * *